United States Patent
Uyama et al.

(10) Patent No.: US 9,056,128 B2
(45) Date of Patent: Jun. 16, 2015

(54) ADJUVANT USED IN DIELECTRIC HEATING-ASSISTED CANCER TREATMENT, AND CANCER TREATMENT METHOD

(75) Inventors: Hirokazu Uyama, Nara (JP); Takamichi Murakami, Osaka (JP); Takashi Imagawa, Kobe (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 1005 days.

(21) Appl. No.: 10/543,895

(22) PCT Filed: Jan. 30, 2004

(86) PCT No.: PCT/JP2004/000907
§ 371 (c)(1),
(2), (4) Date: Jul. 29, 2005

(87) PCT Pub. No.: WO2004/067015
PCT Pub. Date: Aug. 12, 2004

(65) Prior Publication Data
US 2006/0147551 A1    Jul. 6, 2006

(30) Foreign Application Priority Data
Jan. 31, 2003    (JP) .................................. 2003-22993

(51) Int. Cl.
*A61K 9/107*    (2006.01)
*A61K 9/113*    (2006.01)
*A61K 41/00*    (2006.01)

(52) U.S. Cl.
CPC ...................... *A61K 41/00* (2013.01)

(58) Field of Classification Search
USPC ........................................................ 424/400
See application file for complete search history.

(56) References Cited

U.S. PATENT DOCUMENTS

| | | | |
|---|---|---|---|
| 5,120,527 A * | 6/1992 | Li et al. ........................ | 424/9.36 |
| 5,895,653 A * | 4/1999 | Eibl et al. .................... | 424/204.1 |
| 6,174,518 B1 * | 1/2001 | Allard ............................ | 424/59 |
| 6,205,352 B1 | 3/2001 | Carroll | |
| 2001/0002993 A1 * | 6/2001 | Ostensen et al. ............ | 424/9.52 |
| 2002/0064502 A1 | 5/2002 | Gries et al. | |
| 2004/0006336 A1 * | 1/2004 | Swanson ........................ | 606/41 |

FOREIGN PATENT DOCUMENTS

| | | |
|---|---|---|
| EP | 0 444 194 | 9/1991 |
| EP | 0 444 194 A1 | 9/1991 |
| EP | 0 525 199 A1 | 2/1993 |
| EP | 0 913 167 A2 | 5/1999 |
| JP | 55-11509 A | 1/1980 |
| JP | 60-255728 A | 12/1985 |
| JP | 3-128331 A | 5/1991 |
| WO | WO 00/52714 A1 | 9/2000 |
| WO | 02/38546 * | 5/2002 |

OTHER PUBLICATIONS

Moroz et al, Journal of Surgical Oncology, 2001, vol. 78, pp. 22-29.*
Uyama Hirokazu et al., "A Newly Developed Iron and Iodized Oil Emulsion(I-I Emulsion for Enhancing an Effect of Radiofrequency Ablation Therapy of (RFA) of Hepatic Tumor". Database Biosis. Accession No. PREV200300571423 & Digestive Disease Week Abstracts and Itinerary Planner. vol. 2003. p. Abstract No. T1785. May 17-22, 2003.
Moroz Paul et al. "Histologic analysis of liver tissue following hepatic arterial infusion of ferromagnetic particles in a rabbit tumour model". Database Biosis, Accession No. PREV200300215783 & Biometals. vol. 16. No. 3. Sep. 2003, pp. 455-464.
Moroz P. et al.. "Targeting liver tumors with hyperthermia: ferromagnetic embolization in a rabbit liver tumor model". Database Medline. Accession No. NLM11519064 & Journal of Surgical Oncology. Sep. 2001. vol. 78. No. 1, pp. 22-29.
Moroz P. et al.. "The effect of tumour size on ferromagnetic embolization hyperthermia in a rabbit liver tumour model". Database Inspec. Accession No. 7251077 & International Journal Hyperthermia Taylor & Francis Uk. vol. 18, No. 2, 2002. pp. 129-140.
EP Search Report dated Mar. 7, 2006 issued in Application No. 04706842.4.
EP Search Report dated May 30, 2006 issued in Application No, 04706842.4.
Office Action issued in copending Taiwanese Application.
Shina et al, "Predutaneous Radiofrequence Ablation", *Japanese Journal of Cancer* Clinics , 47(11):1081-1088 (2001).
Kudo et al, "Local Treatment of Cancer Cells", *Journal of Clinical and Experimental Medicine*, 200(10):809-811 (2002).
Korean Office Action issued in corresponding Korean Patent Application No. 10-2005-7012800 dated Nov. 3, 2011.

* cited by examiner

*Primary Examiner* — Gollamudi Kishore
(74) *Attorney, Agent, or Firm* — Sughrue Mion, PLLC

(57) ABSTRACT

There is provided an adjuvant capable of enlarging an ablation area and reducing ablation unevenness in a dielectric heating-assisted cancer treatment such as radiofrequency ablation used for treatment of hepatic cancer. The adjuvant includes a conductive substance such as a metal element (e.g., iron) and a pharmaceutically acceptable carrier of lipid dispersion, polymer solution or polymer dispersion.

5 Claims, No Drawings

ADJUVANT USED IN DIELECTRIC HEATING-ASSISTED CANCER TREATMENT, AND CANCER TREATMENT METHOD

CROSS-REFERENCE TO RELATED APPLICATION

This application is a 371 of PCT/JP2004/000907, filed Jan. 30, 2004; the disclosure of which is incorporated herein by reference.

TECHNICAL FIELD

The present invention relates to an adjuvant used in a dielectric heating-assisted cancer treatment, and to a cancer treatment method, and more specifically, to an adjuvant and a cancer treatment method that are capable of widening an ablation area in a radiofrequency ablation which is a kind of local treatment mainly applied for hepatic cancer.

BACKGROUND ART

Recent advances of various kinds of imaging diagnosis technologies have made it possible to diagnose and treat hepatocellular carcinoma at earlier stages. However, in a treatment of hepatocellular carcinoma, frequency of conducting a hepatectomy is often limited for fear of occurrences of complication of cirrhosis and multifocal involvement. For this reason, a number of non-surgery local treatments such as percutaneous ethanol infusion, hepatic arterial embolization, chemical therapy and radiation therapy have been attempted because of their small influence on the hepatic function and easiness of treatment in the case of recurrence, in comparison with hepatectomy.

In order to securely necrose hepatocellular carcinoma, a radiofrequency ablation (hereinafter, referred to as RFA) using a radiofrequency wave (460±5 kHz) has been made into practical use. This therapy ablates cancer cells by causing a tissue to automatically generate frictional heat in response to dielectric heating (see, Syuichiro Shina et al., "Percutaneous radiofrequency ablation", Japanese Journal of Cancer Clinics, Vol. 47, No. 11, p 1081-1088, November 2001; and Masatoshi Kudo, "Local treatment of cancer cells", Journal of Clinical and Experimental Medicine, Vol. 200, No. 10, p809-811, Mar. 9, 2001).

Also, a percutaneous microwave coagulation therapy (hereinafter, referred to as PMCT) has been developed and made into practical use. This method coagulates tumors using a microwave (2450±50 MHz) which is an electromagnetic wave. This method utilizes frictional heat generated by dielectric heating to coagulate tumor tissues. However, the RFA is more frequently used than the PMCT because it leads less complications than the PMCT.

In the RFA, it is often the case that ablation is conducted several times because a sufficient ablation area is not achieved by a single operation. The RFA also has the problems that an ablation area has unevenness because heat is not transferred evenly due to cooling by the blood circulation, and that the incidence of recurrence of cancer largely differs in different facilities.

It is an object of the present invention to provide an adjuvant capable of extending an ablation area and reducing unevenness of ablation mainly in a RFA-assisted ablation of a lesion site.

DISCLOSURE OF THE INVENTION

In diligent study for solving the above problems, inventors of the present invention noticed that a conductive substance such as metal improves the dielectric effect of radiofrequency waves, and newly found that it is possible to ablate and necrose a lesion site like hepatocellular carcinoma over a sufficiently large area that is not achieved heretofore using an usual RFA, when the conductive substance is intravenously or arterially injected in advance, and that unevenness of ablation is also reduced because ablation can be conducted uniformly, and finally accomplished the present invention.

To be more specific, the adjuvant (composition) of the present invention is intended for use in a dielectric heating-assisted cancer treatment, and comprises a conductive substance. Other adjuvant (composition) of the present invention is intended for use in a dielectric heating-assisted cancer treatment, and may comprise a conductive substance and a variety of pharmaceutically acceptable carriers.

As the conductive substance, biocompatible metal elements, such as elements belonging to the eighth group of the periodic table, such as iron elements can be exemplified.

In the present invention, it is especially important for the conductive substance to specifically accumulate in a tumor site. Therefore, in the present invention, it is preferred (1) to use, as the conductive substance, a compound having a suitability to accumulation in tumor site, (2) to use a composition that allows the conductive substance to accumulate in the tumor site, or (3) to use both (1) and (2). In the case of (1), examples of the compound having a suitability to accumulation in a tumor site include colloidal irons such as chelated irons, iron hydroxide colloid, chondroitin sulfate iron and saccharated iron oxide and the like. In the case of (2), for example, in a composition containing a conductive substance and a pharmaceutically acceptable carrier, it is particularly preferred to use a lipid dispersion such as liposome or lipid emulsion, a polymer solution or polymer dispersion of albumin polymer or the like as the carrier.

Additionally, according to the present invention, it is possible to make a conductive substance accumulate in a tumor site via a vein or an artery. When intravenously administered, the conductive substance may be administered in a solution or a colloidal state, preferably having a particle size of not more than 1 µm.

In order to make a conductive substance accumulate in a cancerous tissue more efficiently, it is effective to administer it via an artery which is a nutrient vessel of the cancer. For arterial injection, the adjuvant of the present invention preferably contains a contrast medium such as lipiodol. This enables the adjuvant of the present invention to accumulate in a tumor site, and allows examination of the position or the state of the lesion site by X-ray CT (computerized tomography).

The cancer treatment method of the present invention is characterized by administering a conductive substance into a vein or an artery to cause the conductive substance accumulate in a tumor site, and ablating and necrosing the tumor site by dielectric heating. This cancer treatment method is especially desirable in RFA-assisted ablation treatment of hepatocellular carcinoma.

BEST MODE FOR CARRYING OUT THE INVENTION

The adjuvant of the present invention will now be described in more detail. An adjuvant of the present invention contains a conductive substance. The conductive substance is able to improve the dielectric effect of radiofrequency waves. Accordingly, a sudden drop of heating temperature that would occur as the distance from the electrode needle inserted into a tumor increases can be prevented, and hence the lesion site can be ablated uniformly over a wide area.

As the conductive substance, biologically compatible metal elements can be exemplified. Examples of the metal elements include iron, aluminum, copper, silver and gold, specifically elements belonging to the eighth group of the periodic table, in particular, iron elements being preferably used. The iron elements include various polymeric iron, paramagnetic iron, low-molecular-weight irons, iron oxides, regardless of divalent or trivalent iron. As the form of the compound, simple inorganic salts, organic salts, low-molecular-weight chelates, high-molecular-weight chelates, colloids, covalently bound forms and the like may be acceptable.

The adjuvant (1) of the present invention comprises the aforementioned conductive substance. Preferably, the adjuvant (1) has an ability to accumulate in a tumor site.

Examples of the conductive substance suited for accumulation into a tumor site include colloidal irons such as chelated iron, iron hydroxide colloid, chondroitin sulfate iron and saccharated iron oxide and the like.

The adjuvant (2) of the present invention comprises a conductive substance and a pharmaceutically acceptable carrier. Preferably used carriers include polymer solutions or polymer dispersions of lipid dispersions like lipid emulsion and liposome, $\alpha$, $\beta$ or $\gamma$ dextrin and their derivatives, albumin polymer, polylactic acid/glycol acid, lipoproteins, styrene-maleic acid copolymer, ethylene-propylene copolymer and antibody-bound compounds thereof, to make the conductive substance accumulate in a tumor site.

The lipid emulsion may be oil-in-water type (O/W type) lipid emulsion or water-in-oil-in-water type (W/O/W type) lipid emulsion, for example. The O/W type lipid emulsion may be produced by preparing a crude emulsion by adding oils and fats into a solution of emulsifier dispersed in water, followed by stirring, and emulsifying the resultant crude emulsion by, for example, high-pressure emulsifying method using a homogenizer or the like. Alternatively, the O/W type lipid emulsion may be produced by a membrane emulsifying method using a porous glass membrane having a predetermined pore size.

Examples of the oils and fats include vegetable oils such as soybean oil, cotton seed oil, sunflower oil, corn oil, coconut oil and perilla oil; fish oils such as cod-liver oil; and triglycerides of a variety of fatty acids. Examples of the emulsifier include phospholipids such as lecithin or sphingomyelin; non-ionic surfactants such as polyethylene glycol type or polyol fatty acid ester type. Also, acceptable tonicity agents such as monosaccharides, polysaccharides and glycerin may be used as necessary. Also lipiodol (compound name: iodinized poppyseed oil fatty acid ethyl ester) which is a contrast medium as described later may be used singly or in combination with other oils as an oil phase component.

The conductive substance may be added in any stage in the course of producing the aforementioned lipid emulsion, but preferably it is added together with oils and fats before stirring, and then brought into uniform dispersion by stirring. In the cases where lipid dispersions, polymer solutions, polymer dispersions other than the lipid emulsion are used, the conductive substance should be dispersed uniformly in the carrier using any suitable stirring means.

The particle size of oil drops in an O/W type lipid emulsion is not particularly limited, but preferably 1 μm or less in average particle size. Since the O/W type lipid emulsion has a small average particle size, when it is administered through an artery, it will pass through capillaries to circulate in the body, and finally a large part will accumulate in cancerous cells.

The W/O/W type lipid emulsion can be produced by a two-step membrane emulsifying method using a porous glass membrane, for example. In this method, first, W/O type lipid emulsion is prepared using a first porous glass membrane having a predetermined pore size, and then a W/O/W type lipid emulsion is prepared using a second porous glass membrane having a pore size larger than that of the first porous glass membrane. In the water phase which is an inner water phase, the conductive substance is dispersed. Such two-step membrane emulsifying method is advantageous in that the conductive substance can be accumulated in the lesion site reliably because the particle size of the obtainable emulsion is easy to control and the conductive substance is enclosed in the inner water phase.

Examples of the porous glass membrane include Shirasu porous glass membranes (SPG membranes) that comprise Shirasu porous glass (abbreviated as SPG, product of Miyazaki Industrial Technology Center) or derivatives of Shirasu porous glass that are hydrophobically modified by aminosilanation, octadecylsilylation, trimethylsilylation and the like.

The particle size of oil phase (oil drop) in the W/O/W type lipid emulsion is not particularly limited, but it is preferably 200 μm or less, preferably 100 μm or less in average particle size. The average particle size in the inner water phase within the oil phase is preferably $1/10$ to $1/200$ of that of the oil phase.

Since the W/O/W type lipid emulsion has a large particle size, when it is administered through an artery, it will accumulate in a tumor site.

The content of the conductive substance contained in the adjuvants (1) and (2) of the present invention should be sufficient to provide great benefit of adding the conductive substance when it is accumulated in a tumor site while keeping the conductive substance in a stable manner. Concretely, 1 to 50% by weight of the total amount is appropriate.

The adjuvant of the present invention may contain a contrast medium. As such a contrast medium, contrast media used in the X-ray CT (computerized tomography) can be exemplified, and concretely, lipiodol (compound name: iodinized poppyseed oil fatty acid ethyl ester) and the like can be used. A content of a contrast medium in an adjuvant is sufficient to generate a contrast on the X-ray image between a lesion site in which the adjuvant of the present invention accumulates and other biological tissues. Specifically, a contrast medium is contained in an amount of about 5 to 50% by weight, relative to the total amount of the adjuvant.

Next, how to use the adjuvant of the present invention will be explained while taking the percutaneous RFA as an example. Prior to the RFA, an adjuvant of the present invention is first introduced into a tumor site through a blood vessel. In brief, a catheter is inserted from an arm, leg or the like of the patient into a liver through a blood vessel, thereby making the adjuvant of the present invention accumulate in the tumor site. The position of the catheter is checked by introducing a contrast medium into the catheter. After a pair of opposite polar sheets is respectively adhered to right and left thighs, an electrode needle is percutaneously inserted into a tumor site under the guidance by ultrasound, and then electrification is started. Electrification is achieved by gradually raising the output while keeping the impedance below 90Ω. Then the ablation is conducted for about 12 minutes while the condition of gas generation is observed.

As equipment for the RFA, commercially available equipments from RITA company, RTC company, Radionics company and the like may be used. The equipments from the former two companies use a so-called expandable electrode needle whose tip end circumferentially expands out in a hook shape, and the equipment from the latter one company uses a cool-tip type electrode needle having a needle shape.

When the lesion site has a significant size, the entire lesion site is ablated by introducing an electrode needle into each of several sections of the lesion site. In this case, by making the adjuvant of the present invention containing a conductive substance accumulate in the lesion site, uniform ablation over a wide area is enabled due to improvement of the dielectric effect of the radiofrequency wave. To be more specific, by using the adjuvant of the present invention, it is possible to extend the ablation area for one ablation operation up to about 150%. Therefore, when a large lesion site is treated, the frequency of electrode needle insertion is reduced, and a treatment time is reduced, resulting in reduction of a load on the patient.

Following the treatment, the efficacy of the treatment is determined by evaluation of a necrosis area by CT. At this time, CT determination of the treatment efficacy is facilitated on the condition that the adjuvant of the present invention contains a contrast medium.

In the above explanation, RFA was explained, however, PMCT may also be conducted similarly to RFA. Although the above explanation describes a treatment method of hepatocellular carcinoma, the adjuvant of the present invention may be applied to treatments of other tumors as well as treatment of hepatocellular carcinoma.

INDUSTRIAL APPLICABILITY

According to the present invention, by making an adjuvant comprising a conductive substance or an adjuvant comprising a conductive substance and a carrier accumulate in advance in a lesion site such as hepatocellular carcinoma, it is possible to realize uniform ablation over a wide area using RFA and reduce an ablation unevenness. Therefore, even when the lesion site has a significant size, it is possible to necrose the wide range of lesion site uniformly by a single ablation. As a result, high treatment efficacy is expected, and reduction in treatment time and reduction in load on the patient are realized. The same applies to the case where the adjuvant of the present invention is applied to a PMCT-assisted cancer treatment.

Furthermore, when iron hydroxide colloid or the like is used as a conductive substance, or when an adjuvant comprising a conductive substance and a variety of pharmaceutically acceptable carries is used, greater treatment efficacy is expected because of the excellent ability of the conductive substance to accumulate in a lesion site.

Furthermore, in the present invention, containment of a contrast medium in the adjuvant is advantageous in facilitating the evaluation CT following the treatment.

EXAMPLES

In the following, the present invention will be explained in detail by way of examples, however, the present invention is not limited to the following examples.

Examples 1 to 3

An adjuvant comprising O/W type lipid emulsion was prepared according to the formulation of Table 1. In Table 1, as the iron drug for intravenous injection, "Fesin (Registered Trademark)" (colloidal iron) manufactured by Mitsubishi Pharma Corporation was used. This was an aqueous solution containing saccharated iron oxide, and contained 20 mg of iron per 1 mL. As the contrast medium, lipiodol (Nihon Schering K. K.) was used.

TABLE 1

| Component | Example 1 | Example 2 | Example 3 |
|---|---|---|---|
| Iron drug for intravenous injection | 1 mL | 1 mL | 1 mL |
| Contrast medium | 0.5 mL | 1 mL | — |
| Soybean oil | 500 mg | 500 mg | 500 mg |
| Lecithin | 240 mg | 240 mg | 120 mg |
| Glycerin | 125 mg | 125 mg | 125 mg |
| Distilled water | Reminder | Reminder | Reminder |
| Total amount | 5 mL | 5 mL | 5 mL |

In brief, according to the formulations shown in Table 1, predetermined amounts of iron drug for intravenous injection, contrast medium, soybean oil, lecithin and glycerin were added, and filled up to the total of 5 mL with distilled water, and then emulsified by using a homogenizer. The obtained lipid emulsion (O/W type emulsion) was filtered, and loaded into a glass bottle which was then replaced with nitrogen gas and sealed.

Test Example 1

After placing a healthy pig under anesthesia on an operating table, artificial respiration was given under management of the airway. After managing the circulatory dynamics, an abdominal operation was made. On the other hand, a catheter was inserted from the lower femoral artery, and a contrast medium was introduced, and the catheter was advanced to a proper hepatic artery while the position of the catheter was checked. Then 20 mL of the adjuvant obtained in Example 1 was administered to the liver from this catheter. Then using an RFA apparatus from Radionics corporation, an electrode needle was inserted into the site where the adjuvant was administered, and ablation was conducted until roll-off was achieved.

As to a comparative example (control), ablation was conducted in the same manner as described above except that an adjuvant was not administered.

These two examples were pathologically examined for the degree and region of necrosis of hepatocyte. It was visually observed that necrosis of hepatocyte occurred in wider area when the adjuvant was administered, in contrast to the comparative example.

Test Example 2

10 mL of the adjuvant obtained in Example 1 was mixed into albumen of hen egg, and ablation using an RFA apparatus of RITA corporation was conducted while inserting an electrode needle into albumen.

As to a comparative example (control), ablation of albumen was conducted in the same manner as described above except that an adjuvant was not administered. Then coagulation weight of albumen was compared between these examples. The result is shown in Table 2. The result shows that coagulation weight of albumen increased to about 150% as a result of administration of the adjuvant.

TABLE 2

|  |  | Coagulation weight of albumen (g) |
|---|---|---|
| Adjuvant of the present invention | (1) | 26.56 |
|  | (2) | 24.87 |
|  | Average value | 25.72 |
| Control group | (1) | 15.52 |
|  | (2) | 19.11 |
|  | Average value | 17.32 |

These results showed that the ablation area can be enlarged by a single ablation by using the adjuvant of the present invention.

Example 4

A W/O/W type lipid emulsion having the composition shown below and enclosing the above "Fesin" (colloidal iron) in an inner water phase was prepared.

| (1) Inner water phase | 3 mL of Fesin solution diluted to 5 times with water for injection (Fe 4 mg/mL) |
|---|---|
| (2) Oil phase | 5 mL of lipiodol |
| (3) Oil phase emulsifier | 0.25 g of TGCR-310 |
| (4) Outer water phase | 7 mL of 1% by weight of "HCO-60" + 5% by weight of glucose |

In brief, after adding 0.25 g of TGCR-310 (tetraglycerol polyrecinolate, manufactured by Sakamoto Yakuhin Kogyo Co., Ltd.) to 5 mL of lipiodol (contrast agent) put in a sample bottle, a stirrer was put into the bottle and stirring was conducted at about 1000 rpm. 3 mL of Fesin diluted solution was put into another syringe, and a SPG membrane having a pore size of 5 μm was attached to the tip end of the syringe. Then the Fesin dilution was gradually added (5 mL/hour) to the lipiodol under stirring through an SPG membrane, to obtain a $W_1/O$ type lipid emulsion.

Almost the entire of this $W_1/O$ type lipid emulsion was collected in a syringe, and an SPG membrane having a pore size of 20 μm was attached to the tip end of the syringe. 7 mL of an outer water phase solution containing 1% by weight of HCO-60 (polyoxyethylene POE(60) hydrogenated caster oil) and 5% by weight of glucose was gradually added (10 mL/hour) to the $W_1/O$ type lipid emulsion through the SPG membrane under stirring at about 1000 rpm, to obtain a $W_1/O/W_2$ type lipid emulsion as an adjuvant.

The obtained $W_1/O/W_2$ type lipid emulsion included oil drops having an inner water phase and average particle size of 50 to 100 μm, and the particle size distribution was relatively narrow. The $W_1/O/W_2$ type lipid emulsion was stable with no release of iron molecules into the outer water phase, and no temporal change of particle size.

The invention claimed is:

1. A method for treating an hepatic tumor comprising:
injecting the hepatic tumor with a pharmaceutical composition that comprises an oil-in-water emulsion consisting of a liquid oil phase and a liquid water phase at body temperature, wherein the liquid oil phase is selected from the group consisting of vegetable oils, fish oils, and triglycerides, and wherein the liquid water phase comprises a conductive substance in an effective amount up to about 0.5% (w/v);
accumulating the conductive substance of the adjuvant at the site of the hepatic tumor; and
administering radiofrequency ablation therapy to necrose the hepatic tumor,
wherein the conductive substance is selected from the group consisting of iron hydroxide, chondroitin sulfate iron and saccharated iron oxide, and
wherein the presence of the conductive substance at the site of the hepatic tumor augments the region of necrosis by enhancing frictional heat generated by dielectric heating.

2. The method according to claim 1, further comprising:
administering a contrast medium into an artery or a vein of the subject.

3. A method of treating an hepatic tumor comprising:
injecting the hepatic tumor with a pharmaceutical composition that comprises an oil-in-water emulsion consisting of a liquid oil phase and a liquid water phase at body temperature, wherein the liquid oil phase is selected from the group consisting of vegetable oils, fish oils, and triglycerides, and wherein the liquid water phase comprises a conductive substance in an effective amount up to about 0.5% (w/v);
accumulating the conductive substance of the adjuvant at the site of the hepatic tumor; and
administering microwave coagulation therapy to necrose the hepatic tumor,
wherein the conductive substance is selected from the group consisting of iron hydroxide, chondroitin sulfate iron and saccharated iron oxide, and
wherein the presence of the conductive substance at the site of the hepatic tumor augments the region of necrosis by enhancing frictional heat generated by dielectric heating.

4. A method for treating an hepatic tumor comprising:
injecting the hepatic tumor with a pharmaceutical composition comprising an adjuvant;
accumulating the conductive substance of the adjuvant at the site of the hepatic tumor;
administering radiofrequency ablation therapy to necrose the hepatic tumor,
wherein the presence of the conductive substance at the site of the hepatic tumor augments the region of necrosis by enhancing frictional heat generated by dielectric heating, and
wherein the adjuvant is:
(1) an injectable adjuvant consisting of:
a water-in-oil-in-water emulsion; and optionally a contrast agent, wherein the emulsion consists of an outer liquid water phase, a liquid oil phase and an inner liquid water phase at body temperature;
wherein the inner liquid water phase of the water-in-oil-in-water emulsion comprises a conductive substance;
wherein the conductive substance is selected from the group consisting of iron hydroxide, chondroitin sulfate iron and saccharated iron oxide; and
wherein the conductive substance is not present in the outer liquid water phase, or
(2) an adjuvant consisting of an effective amount of an injectable pharmaceutical composition effective at uniformly enlarging an area of necrosis caused by heat ablation therapy of the hepatic tumor wherein the composition comprises:
a water-in-oil-in-water emulsion consisting of an outer liquid water phase, a liquid oil phase and an inner liquid water phase at body temperature;
wherein the liquid oil phase is selected from the group consisting of vegetable oils, fish oils, and triglycerides;

wherein the inner liquid water phase comprises a conductive substance;
wherein the conductive substance is selected from the group consisting of iron hydroxide, chondroitin sulfate iron and saccharated iron oxide; and
wherein the conductive substance is not present in the outer liquid water phase.

5. A method of treating a hepatic tumor comprising:
injecting the hepatic tumor with a pharmaceutical composition comprising an adjuvant;
accumulating the conductive substance of the adjuvant at the site of the hepatic tumor; and
administering microwave coagulation therapy to necrose the hepatic tumor,
wherein the presence of the conductive substance at the site of the hepatic tumor augments the region of necrosis by enhancing frictional heat generated by dielectric heating, and
wherein the adjuvant is:
(1) an injectable adjuvant consisting of a water-in-oil-in-water emulsion; and
optionally a contrast agent wherein the emulsion consists of an outer liquid water phase, a liquid oil phase and an inner liquid water phase at body temperature;
wherein the inner liquid water phase of the water-in-oil-in-water emulsion comprises a conductive substance;
wherein the conductive substance is selected from the group consisting of iron hydroxide, chondroitin sulfate iron and saccharated iron oxide; and
wherein the conductive substance is not present in the outer liquid water phase, or
(2) an adjuvant consisting of an effective amount of an injectable pharmaceutical composition effective at uniformly enlarging an area of necrosis caused by heat ablation therapy of the hepatic tumor, wherein the composition comprises a water-in-oil-in-water emulsion consisting of an outer liquid water phase, a liquid oil phase and an inner liquid water phase at body temperature;
wherein the liquid oil phase is selected from the group consisting of vegetable oils, fish oils, and triglycerides;
wherein the inner liquid water phase comprises a conductive substance;
wherein the conductive substance is selected from the group consisting of iron hydroxide, chondroitin sulfate iron and saccharated iron oxide; and
wherein the conductive substance is not present in the outer liquid water phase.

* * * * *